United States Patent [19]

Huang et al.

[11] Patent Number: 5,445,954
[45] Date of Patent: Aug. 29, 1995

[54] SYSTEM FOR AUTOMATIC GENE AMPLIFICATION AND EXPRESSION

[75] Inventors: Ru C. Huang; Paul E. Giza, both of Baltimore, Md.

[73] Assignee: The Johns Hopkins University, Baltimore, Md.

[21] Appl. No.: 16,188

[22] Filed: Feb. 11, 1993

Related U.S. Application Data

[63] Continuation of Ser. No. 356,299, May 24, 1989, abandoned.

[51] Int. Cl.⁶ .................... C12N 15/70; C12N 15/74; C12N 15/69
[52] U.S. Cl. .................. 435/252.33; 435/69.1; 435/172.1; 435/172.3; 435/252.3; 435/252.31; 435/320.1
[58] Field of Search ................. 435/69.1, 172.1, 172.3, 435/320.1, 252.3, 252.31, 252.33

[56] References Cited

U.S. PATENT DOCUMENTS 4,374,927  2/1983  Sninsky et al. ................ 435/69.1

OTHER PUBLICATIONS

Fitzwater et al. EMBO J. 7(10):3283 (1988).
Maniatis et al Molecular cloning, CSH (1982).
Wu et al. J Bact. 1985. 163(3):973.
Giza et al. Gene 78(1989), pp. 73–84.

*Primary Examiner*—Jacqueline Stone
*Assistant Examiner*—J. Leguyader
*Attorney, Agent, or Firm*—Cushman Darby & Cushman

[57] ABSTRACT

Discoveries are disclosed that show that certain mutations in different parts of the mechanism for regulation of independently replicating element replication can be combined in one expression independently replicating element to produce a runaway-replication phenotype that is suppressible by a diffusible factor from another independently replicating element co-resident in the host cell. According to the present invention, an expression independently replicating element combining known inducible promoters with this runaway-replication phenotype is used in combination with a independently replicating element that suppresses this runaway phenotype to establish a gene expression system that provides both controllable gene amplification and controllable induction of gene expression without the use of chemical inducers or temperature shifts. This expression system produces high yields of proteins in readily isolatable forms.

4 Claims, 5 Drawing Sheets

FIG. 3

Rop protein: 63 aa; 7.2 kDa

PvuII
CGCAGCTGCCTCGCGCGTTTCGGTGATGACGGTGAAAACCTC
ArgSerCysLeuAlaArgPheGlyAspAspGlyGluAsnLeu
50          55          60

CGCAGCGGTGAGCGTGGGTCTCGCGGTATCATT          pRop-404
ArgSerGlyGluArgGlySerArgGlyIleIle          102; 11.4
50          55          60

CGCAGAATTCCCGGGGATCCGTCGATGGACCCC          pRop-MT
ArgArgIleProGlyAspProSerMetAspPro          118; 12.6
50          55          60

CGCAGAATTCCCGGGGATCCGTCGATGAATCAC          pRop-MT(opp)
ArgArgIleProGlyAspProSerMetAsnHis          73; 8.5
50          55          60

CGCAGCTGCATGGAGCCAGTAGATCCTAGACTA          pRop-Tat
ArgSerCysMetGluProValAspProArgLeu          138; 15.8
50          55          60

CGCAGCATGGATCCCGCCGTCTCCCCCGCGAGC          pRop-HSV 38K
ArgSerMetAspProAlaValSerProAlaSer          388; 43.6
50          55          60

SYSTEM FOR AUTOMATIC GENE AMPLIFICATION AND EXPRESSION

This is a continuation of application Ser. No. 0 7/356,299, filed on May 24, 1989, now abandoned.

FIELD OF THE INVENTION

The present invention relates to genetic expression systems that provide automatic sequential induction of both gene amplification and gene expression without the use of chemical inducers or temperature shifts. More specifically, this invention relates to expression systems comprising a first independently replicating genetic element which exhibits a runaway-replication phenotype that can be suppressed by a diffusible factor supplied by a second independently replicating element. This first element also includes a site for insertion of a gene to be expressed wherein expression of an inserted gene is under the control of a promoter that is negatively regulated by a repressor. As a result of runaway replication of this first element, this system provides induction of this negatively regulated promoter and, consequently, expression of an inserted gene. This invention also relates to methods for the synthesis and isolation of products of genes by recombinant cells containing the expression system of this invention.

BACKGROUND OF THE INVENTION

Many systems have been developed for expression of genes which encode products of commercial interest. For various purposes, such genetic expression systems frequently employ genetic elements that have the capacity to replicate when separated from the genome of the host cell in which they replicate and, accordingly, may be designated as independently replicating genetic elements. Independently replicating elements used in expression systems comprise, for example, variants of DNA or RNA virus genomes including proviruses. Such elements further comprise nonviral genomes that are typically encoded in circular DNA molecules including plasmids.

It is well known in the art that the level of production of a protein by a cell usually is increased substantially by increasing the number of copies per cell of the gene encoding that protein. Therefore, many gene expression systems include a means for providing multiple copies in each host cell of the gene for the desired protein, in other words, a means for amplifying the DNA encoding the desired gene.

Certain observations about replication of bacterial plasmids, for example, have been exploited for the purpose of gene amplification in genetic expression systems. In particular, plasmids occurring in several bacteria in nature possess genetic mechanisms for regulating their replication. These regulatory mechanisms maintain plasmid replication in concert with that of the host cell. Genetic variants of plasmids are known that exhibit different ratios of the number of plasmid copies to the number of host cell genomes per cell under typical cell growth conditions. Thus, the so-called "copy number" is a genetically determined attribute (i.e., a "phenotype") of a given independently replicating element such as a plasmid.

Some plasmids are typified by an unconditional "high-copy-number" phenotype, which is useful for providing limited gene amplification in bacterial expression systems. Even more useful for gene amplification are certain conditional mutants of plasmids which suffer complete abrogation of genetic regulatory restraints on plasmid replication. These mutants express or exhibit uncontrolled plasmid replication that outstrips or runs away from the replication of the host cell genome. Accordingly, a phenotype characterized by such uncontrolled replication is known in the art as a "runaway-replication" phenotype. (Such a phenotype may also be called a "runaway-copy-number" phenotype.)

Continuous expression of a runaway-replication phenotype results in excessive plasmid accumulation that ultimately leads to death of the host cell. However, temperature-sensitive (ts) mutations affecting regulation of plasmid replication are known which exhibit a conditional (more specifically, a temperature-dependent) runaway-replication phenotype that is particularly useful for gene amplification in expression systems. Under the appropriate environmental conditions (i.e., below a critical temperature), replication of ts runaway-replication plasmids is sufficiently limited to allow continuous cell growth. Above that critical thermal point, however, such plasmids accumulate in the cell in amounts far beyond the levels achievable with plasmids of unconditional high-copy-number, which necessarily must not accumulate in lethal amounts. Use of a plasmid for gene expression that exhibits a conditional runaway-replication phenotype thus allows greater plasmid accumulation and, hence, greater amplification of any gene inserted into that plasmid, than can be obtained using a plasmid with an unconditional high-copy-number phenotype.

A more detailed understanding of the genetic basis of regulation of plasmid replication in general, and particularly of runaway-replication phenotypes, especially in specific plasmids of *Escherichia coli* (hereinafter, *E. coli*), will be helpful for appreciation of the workings of the present invention. Regulation of plasmid replication has been studied most extensively, in fact, in *E. coli*, in a group of plasmids related to a prototype known as the ColIE plasmid.

It has long been established that to replicate as an independent DNA molecule, any independently replicating element requires specific sequences for initiation of DNA replication that are designated the "origin of replication". This origin provides a recognition site for an RNA polymerase (i.e., a promoter) to begin de novo synthesis of an RNA strand complementary to a short sequence of DNA adjacent to the promoter. The resulting short RNA, which is called the "primer" for DNA synthesis, is then extended by a DNA polymerase to form an long DNA strand covalently linked with the RNA primer. This indirect method of initiating DNA replication via RNA synthesis appears to be necessary because the DNA polymerase cannot initiate a new strand but can only extend existing polynucleotides.

Further, the requirement for RNA synthesis to initiate DNA replication provides a means for regulation of plasmid replication involving the RNA primer and a small RNA called "RNA I". RNA I is transcribed from the antisense strand of DNA in the region encoding the primer (which historically has been designated as "RNA II"; Lacatena, R. M., et al, 1984, Cell 37, 1009–1014; Tomizawa, J. et al, 1986, Cell 47, 89–97). Binding between RNA I and RNA II leads to transcription termination, thereby preventing DNA synthesis at the origin of replication. More specifically, RNA I is thought to exert its negative control on plasmid copy number through the base pairing interactions of its particular structural features called "stem-loops" with similar stem-loop structures of the primer transcript (Davison, J., 1984, Gene 28, 1–15; Cesareni, G. et al, 1985, Trends Biochem. Sci. 10, 303–306; Wong, E. M. et al, 1985, Cell 42, 959–966; Tomizawa, J. et al, 1986, Cell 47, 89–97).

The conditional runaway-replication phenotype of some plasmids used for gene expression in E. coli derives from ts mutations in the primer transcript (RNA II) that cause elevated copy number when cells harboring the plasmid are grown at a temperature higher than some critical temperature. Several gene expression systems are known that combine the features of a particular thermoinducible runaway plasmid, for example, pKN402 (Uhlin, B. E. et al, 1979, Gene 6, 91–106) with those of efficient promoters, to produce high-level expression in bacteria (Bittner, M. et al, 1981, Gene 15, 319–329; Masui, Y., et al, 1983, Academic Press, New York, N.Y., pp. 15–32; Remaut et al., 1983, Gene 22, 103–113). Another example of a runaway plasmid useful for gene expression is the 7.3 kb plasmid pEW2762 (Wong et al., 1982, Proc. Natl. Acad. Sci. USA 79, 3570–3574) which contains two ts mutations in the particular stem-loop of the primer transcript (RNA II) designated stem-loop IV. Together these two ts mutations cause elevated copy number when cells harboring the plasmid are grown at 42 C., but do not adversely affect regulation of plasmid replication at 30 C. (Wong et al., 1982, Proc. Natl. Acad. Sci. USA 79, 3570–3574; Wong and Polisky, 1985, Cell 42, 959–966). It is presumed that these ts mutations act by changing the conformation of RNA II, in a temperature-dependent manner, so that at elevated temperatures only, RNA II cannot bind RNA I. This temperature-sensitive copy-number phenotype of the plasmid bearing such ts primer mutations has been designated the $Cop^{ts}$ phenotype.

It is also noteworthy in relation to the present invention that the regulation of replication in at least some plasmids is further influenced by diffusible factors encoded by the plasmid. One particularly relevant example of such a factor is a small plasmid-encoded protein known as Rop which is found in some ColE1 and ColE1-like plasmids. This protein was named 'repressor of primer', or Rop, because of its evident ability to regulate transcription initiation at the promoter for the RNA primer in the plasmid origin of replication; for example, this protein reduced β-galactosidase production to background levels when the lacZ gene was placed under the control of the replication primer promoter (Cesareni et al., 1982, Natl. Acad. Sci. USA 79, 6313–6317). Subsequent research has shown that Rop acts in concert with RNA I to negatively regulate copy number. More specifically, Rop influences plasmid copy number by enhancing or modulating the binding between the primer transcript (RNA II) and RNA I. Because of this modulatory effect of Rop on the RNA I-RNA II interaction, some researchers refer to this protein as Rom ('RNA one [inhibition] modulator'; Tomizawa and Som, 1984, 1984, Cell 38, 871–878). Although details of the role of Rop in plasmid replication are not completely understood, it is thought that loss of Rop alone may produce a high-copy-number phenotype but not a runaway-replication phenotype as distinguished herein. More extensive reviews of how Rop function controls plasmid copy number have been published (Davison, J., 1984, Gene 28, 1–15; Cesareni, G. et al, 1985, Trends Biochem. Sci. 10, 303–306).

Although regulation of plasmid replication has not been as extensively studied in many systems outside of E. coli, it is notable in connection with the potential application of the present invention that there is a gene called rep in Bacillus subtilis that appears to be analogous to the rop gene (i.e., the gene which encodes the Rop protein) in E. coli.

It may also be noted here that in the art there is known a general strategy, which has been used by several investigators, for identifying those runaway-replication mutations in plasmid regulatory sequences that affect a diffusible factor (Shepard et al., 1979, Cell 18, 267–275; Twigg and Sherrat, 1980, Nature 283, 216–218). This strategy involves testing the ability of a second plasmid, which is co-resident in the same cell as the mutant plasmid, to suppress the lethal effects of the runaway-replication mutation by supplying the normal form of the factor that is affected by the runaway mutation. Thus, there is a readily utilizable testing scheme for identification, in plasmids or in other independently replicating genetic elements, of mutations that exhibit a conditional runaway-replication phenotype that is suppressible by a diffusible factor.

Besides the above particulars on the regulation of plasmid replication, certain other aspects of the art of gene expression systems are relevant to comprehension of the present invention. For instance, it is well known that production of some foreign proteins in bacterial or other host cells is lethal to those cells; or, in any case, the highest possible expression of any gene at the least limits the ability of the cells to grow rapidly and to reach high densities under practical conditions. Therefore, many expression systems designed for high level protein production utilize some form of inducible gene expression mechanism that can be controlled by environmental conditions. This be controlled by environmental conditions. This inducible mechanism serves to eliminate or minimize production of the desired protein during growth of the cells until sufficient cell mass and optimum cell density for the needed level of protein production are obtained. At that point, gene expression is induced by some environmental stimulus, typically by means of adding some chemical inducer or by suddenly raising the temperature of the culture by several degrees. Thus, the use of an inducible gene expression system optimizes overall yield by minimizing inhibitory effects on cell growth caused by the actual production of the desired protein.

Certain gene expression systems are known that combine the advantages of inducible runaway plasmid replication, for increasing gene copy number, with those of inducible gene expression, for minimizing interference with cell growth. For example, a system may include multiple ts mutations, in both copy number control and gene expression control functions. In a plasmid including temperature-dependent means for inducing both runaway replication and expression of the desired protein, both of these functions are inhibited during growth of the cells at a lower than normal temperature. Raising the culture temperature a few degrees, however, inactivates inhibitory factors for both functions, thereby simultaneously inducing both runaway plasmid replication and high level expression of the desired gene product.

In temperature-inducible gene expression systems, a ts mutation affecting expression of the gene for the desired protein typically lies in a regulatory gene encoding a repressor protein that inhibits transcription initiation at a particular promoter element. This promotor is located in the plasmid so that it controls expression of any gene of interest that is inserted in the plasmid in the appropriate manner.

Other expression systems combine heat-inducible runaway plasmids with alternative means for inducible gene expression, such as a promoter and associated repressor that are regulated by a chemical inducer. For example, some chemically inducible expression systems employ a promoter which normally functions in a bacterial cell in the conditional regulation of genes for a biochemical pathway that provides an essential nutrient such as an amino acid. Such an inducible promoter serves to shut down production of the enzymes needed for synthesis of that amino acid when that nutrient is present in the extracellular environment at concentrations sufficient to sustain bacterial growth, thereby conserving resources that would otherwise be expended needlessly on unnecessary metabolic capacity. When the relevant amino acid is depleted from the environment, the repressor of such an inducible gene expression system becomes less able to inhibit transcription initiation from its related promoter; accordingly, expression of any genes under the control of this promoter is induced by the removal of the critical amino acid from a culture.

In practice, however, exhaustive depletion from growth medium of a nutrient, such as an amino acid, is difficult to achieve in any case. This depletion is particularly difficult to achieve in a readily controllable fashion that permits gene expression to be induced efficiently in large scale cultures at an optimum cell density without undue manipulations (e.g., changing the culture medium) that may interfere with protein production. It is advantageous for inducible gene expression, therefore, to exploit the well known observation that repressors of certain chemically regulated promoters may respond to the presence of some intermediary metabolite as well as to the absence of the product of the inducible biochemical pathway which is regulated by that promoter and repressor.

For instance, the promoter for the complex of genes involved in tryptophan synthesis (i.e., the trp promoter) is subject to dual chemical regulation and is frequently employed in inducible gene expression systems, due in large measure to its inherent propensity for high levels of transcription of any associated gene. Although inhibition of this promoter by its repressor is attenuated in the absence of tryptophan, more complete induction of the promoter is obtained in the presence of an intermediate in the tryptophan synthetic pathway. This intermediate is produced by control of the trp promoter. Therefore, as tryptophan is depleted from a culture, normally the synthetic pathway enzymes are partially induced; the metabolic intermediate produced by the pathway then more fully blocks the action of the repressor and thereby completely induces the trp promoter. In practice, induction of expression of genes under the control of the trp promoter is most efficiently and fully achieved, even in the presence of low levels of tryptophan, by the addition of a nonmetabolizable analog of the relevant intermediary metabolite.

In the use of bacterial expression systems that combine temperature-dependent regulation of plasmid copy number with chemical regulation of gene expression, when the cells have reached an optimum density, the increase in plasmid copy number (i.e., "gene amplification") may be carried out prior to induction of expression of the desired gene product, thereby minimizing possible inhibitory effects of that gene expression on the gene amplification process. After plasmid accumulation has reached an optimum level for protein production, the an optimum level for protein production, the inducible promoter may be activated by addition of the necessary chemical inducer.

The abrupt environmental changes needed for efficient induction of most gene expression systems pose considerable engineering problems for production of proteins in large scale cultures that are required for many commercial purposes. For example, many ts mutations in repressor proteins are expressed (i.e., become effective by inactivating the repressor) upon a shift in cell temperature from a low temperature (e.g., about 30 C.) to a higher temperature (e.g., in the range of 37 to 42 C.). If gene expression is to be fully induced by temperature shift while maintaining a particular cell density, then the shift must be completed well within the time required for a cell replication cycle, typically on the order of half an hour in the operative temperature range.

Further, incubation for a few minutes at temperatures slightly higher than 42 C. (e.g., 5 to 10 minutes at 45 C.) is actually beneficial for achieving complete inactivation of some ts mutant repressors. On the other hand, more prolonged incubation of cells under these conditions, or even brief exposure to higher temperatures, begins to kill cells, resulting in rapid loss of protein production capacity in the culture. Since it is difficult to design and operate large scale culturing equipment which is capable of the rapid and accurate control of the temperature shifts demanded by ts repressor mutants for optimum performance, the use of such heat inducible gene expression systems is problematic for applications requiring more than a few liters of culture.

Although not all ts mutations in repressor genes or in plasmid copy number control genes require the precise up-and-down regimen of temperature shifts outlined above, nevertheless, even the less demanding task of raising the temperature relatively rapidly without excessive temperature excursions beyond tolerable limits is formidable in large scale cultures. The use of a chemically inducible gene expression system reduces the engineering problems associated with precise control of gene induction by temperature shift and allows separate control of gene amplification and expression; nevertheless, substantial equipment for rapid and thorough admixing of the added inducer must be provided.

In conclusion, although many genetic expression systems already have exploited inducible promoters for controlling gene expression, either alone or in combination with inducible runaway-replication plasmids, virtually all such inducible systems suffer from the general problems that the environmental stimulus required for induction is difficult to provide in large scale cultures, and that the process of providing the inducing stimulus may interfere with protein production.

Accordingly, a major object of the present invention is to provide genetic expression systems for producing proteins at consistently high yields and on scales suitable for commercial purposes, that are inducible without temperature shifts, chemical inducers, or specialized cell growth medium. The present invention contemplates utilization of novel combinations of genetic alterations that produce a runaway-replication phenotype with particular characteristics, together with other approaches for inducible gene expression and protein production, to achieve this major object and other related objects of this invention that are described below.

SUMMARY OF THE INVENTION

It has now been discovered that certain mutations in different parts of the mechanism for regulation of plasmid replication, when combined in one plasmid, exhibit a runaway-replication phenotype with unusual properties that have enabled in large measure one of the primary aspects of the present invention. In particular, this phenotype is suppressed by a diffusible factor from another plasmid that is co-resident in the host cell, despite the fact that none of the responsible mutations alone produces such a suppressible runaway phenotype. Further, in the absence of the suppressing factor, this runaway phenotype is not temperature-dependent, despite the fact that some of the mutations in the combination responsible for this novel phenotype are temperature-sensitive.

This suppressible runaway-replication phenotype is used in the present invention to provide a means for induction of runaway replication of an independently replicating genetic element used for gene expression and, hence, for induction of amplification of any gene inserted therein. According to this aspect of this invention, this first independently replicating element is maintained in a host cell by means of a selectable genetic marker. A second independently replicating element, which supplies the factor that suppresses the runaway-replication phenotype of the first independently replicating element, is maintained in the host cell by means of a different selectable marker.

In the following discussion, terms and attributes related to a particular form of independently replicating genetic element, namely a plasmid, are used conveniently for illustrative purposes without implying any limitation of the scope of the present invention this particular type of independently replicating element. Typical selectable markers for maintenance of plasmids in host cells are genes that confers upon the cell resistance to an antibiotic that is present in the culture growth medium. In the practice of this present invention using plasmids, as long as the host cell culture medium contains selection agents for both markers, only cells containing both the first and second plasmids survive and replicate, and runaway replication of the first (expression) plasmid is suppressed by the co-resident plasmid.

On the other hand, when a culture of cells containing co-resident plasmids is simply diluted with ordinary growth medium containing only the one selection agent required to maintain the expression plasmid, the second plasmid is gradually lost from the culture according to a mechanism that is well known in the art. [In brief, despite the fact that the second plasmid continues to replicate in the absence of its selection agent, through random plasmid distribution during partitioning of the dividing cells, some cells lacking the second plasmid will arise; and, relieved of the burden of replicating the second plasmid, these cells will eventually dominate the culture.] Accordingly, in the cells that have lost the second plasmid, the existing suppression factor for the runaway-replication phenotype is no longer replenished and becomes diluted as the cells continue to divide. Eventually, the level of this factor is insufficient to suppress the runaway-replication phenotype, and the expression plasmid, including any inserted gene, begins to be amplified. Thus this unusual, suppressible runaway-replication phenotype is employed in the present invention to provide induction of gene amplification, in essence, merely by diluting a seed culture into a larger volume of ordinary growth medium, as is customary procedure in generating large scale cell cultures.

The present invention also provides a means for inducing expression of the desired gene after amplification of the expression plasmid as described above. For this purpose, the expression plasmid also provides a site for insertion of any gene to be expressed situated so that an inducible promoter controls expression of any gene inserted therein. This inducible promoter is subject to negative regulation by a protein whereby initiation of transcription is inhibited when this regulatory protein binds to sequences near this promoter. The regulatory protein in such a negative regulation scheme is commonly called a repressor protein.

In the present invention, moreover, the gene for the repressor protein that inhibits transcription initiation at the gene expression promoter is not located on the expression plasmid; instead it may be advantageously located on the host cell genome. When the expression plasmid becomes amplified according to the practice of this invention, eventually the concentration of the gene expression promoter exceeds that of its repressor. (In other words, the repressor is overcome by "titration" with excess promoter-related binding sites.) Therefore, transcription of the inserted gene is initiated at the inducible expression promoter consequent to the runaway plasmid replication that was previously induced by the dilution of the culture for expansion to large scale.

In short, the expression system of the present invention may be thought to provide automatic sequential induction of both gene amplification and gene expression once ordinary culture medium is seeded with an appropriate inoculum of cells comprising this system.

In a preferred embodiment of the instant invention in an *E. coli* expression system, the site for insertion of a gene to be expressed in the first plasmid, which is under control of the inducible promoter, lies within the gene encoding the Rop protein which, therefore, is likewise controlled by the gene expression promoter. Accordingly, in this case, the system is operated by fusing the gene encoding the desired protein product to the rop gene. This fusion step serves to accomplish two distinct objectives: it inactivates the Rop function, thereby generating the suppressible runaway-replication phenotype of this invention; and more important, this fusion step also simultaneously renders the desired product in an advantageous form for isolation in high yields, to wit, in an insoluble fusion protein that contains additional amino acids of the Rop protein.

In light of the above explanations of various aspects of the instant invention, the following serves as a concise summary of the main features of this invention. The present invention relates to a genetic expression system comprising two independently replicating elements and additional genetic constituents as follows. The first independently replicating element includes a site for insertion of a gene to be expressed wherein expression of the inserted gene is under the control of a negatively regulated promoter. In addition, the first independently replicating element also includes a selectable marker for maintenance of that element in a host cell. Further, this first independently replicating element exhibits a runaway-replication phenotype that is suppressed by a diffusible factor. This expression system further comprises a second independently replicating element that includes a gene that expresses the diffusible factor that suppresses the runaway-replication phenotype of the first element. This second element also includes a selectable marker for maintenance of this second element in the host cell that is different from the marker of the first element. Finally, this system further comprises a gene that expresses a repressor of the negatively regulated promoter for expression of an inserted gene, this repressor gene being located on a genome other than the first genetic element, for instance, on the host cell genome.

In a major embodiment of this aspect of the present invention, in the first independently replicating element the site for insertion of a gene to be expressed is located within the gene for the diffusible factor that suppresses the runaway-replication phenotype of the first element. Insertion of any gene sequence in this site causes the runaway-replication phenotype of the first element to be exhibited. This gene insertion site is further selected to provide insertion of the gene to be expressed in the translational reading frame of the gene for the diffusible factor.

In a most preferred embodiment, the diffusible factor that suppresses the runaway-replication phenotype is a protein that modulates inhibition of replication of the first element by interacting with the RNA primer for replication of that first element. The product of the rop gene of E. coli exemplifies such a most preferred diffusible factor in a bacterial plasmid. Further, in this most preferred embodiment, the gene insertion site is under control of the trp promoter and is located within the rop gene and is further selected to provide an insoluble fusion protein that contains the product of gene to be expressed fused to additional amino acids of the Rop protein.

The first plasmid in this most preferred embodiment of this aspect of the invention is exemplified in E. coli by either of the two plasmids, pPGtrpRopAp or pPGtrpRopTc, further comprising a gene to be expressed inserted in the rop gene, while the second plasmid is typified by the other of the two plasmids, pPGtrpRopAp or pPGtrpRopTc, wherein the rop gene is intact.

This invention also relates to cultures of recombinant cells containing an expression system of this invention, and to methods for the synthesis and isolation of products of genes by recombinant cells containing the bacterial expression system of this invention.

The present invention may be understood more readily by reference to the following detailed description of specific embodiments and the Examples and Figures included therein.

BRIEF DESCRIPTION OF THE FIGURES

FIG. 3. The nucleotide and amino acid sequences at the fusion points resulting from insertion of various genes into the rop gene of the expression plasmid.

DESCRIPTION OF SPECIFIC EMBODIMENTS

Figure 1:
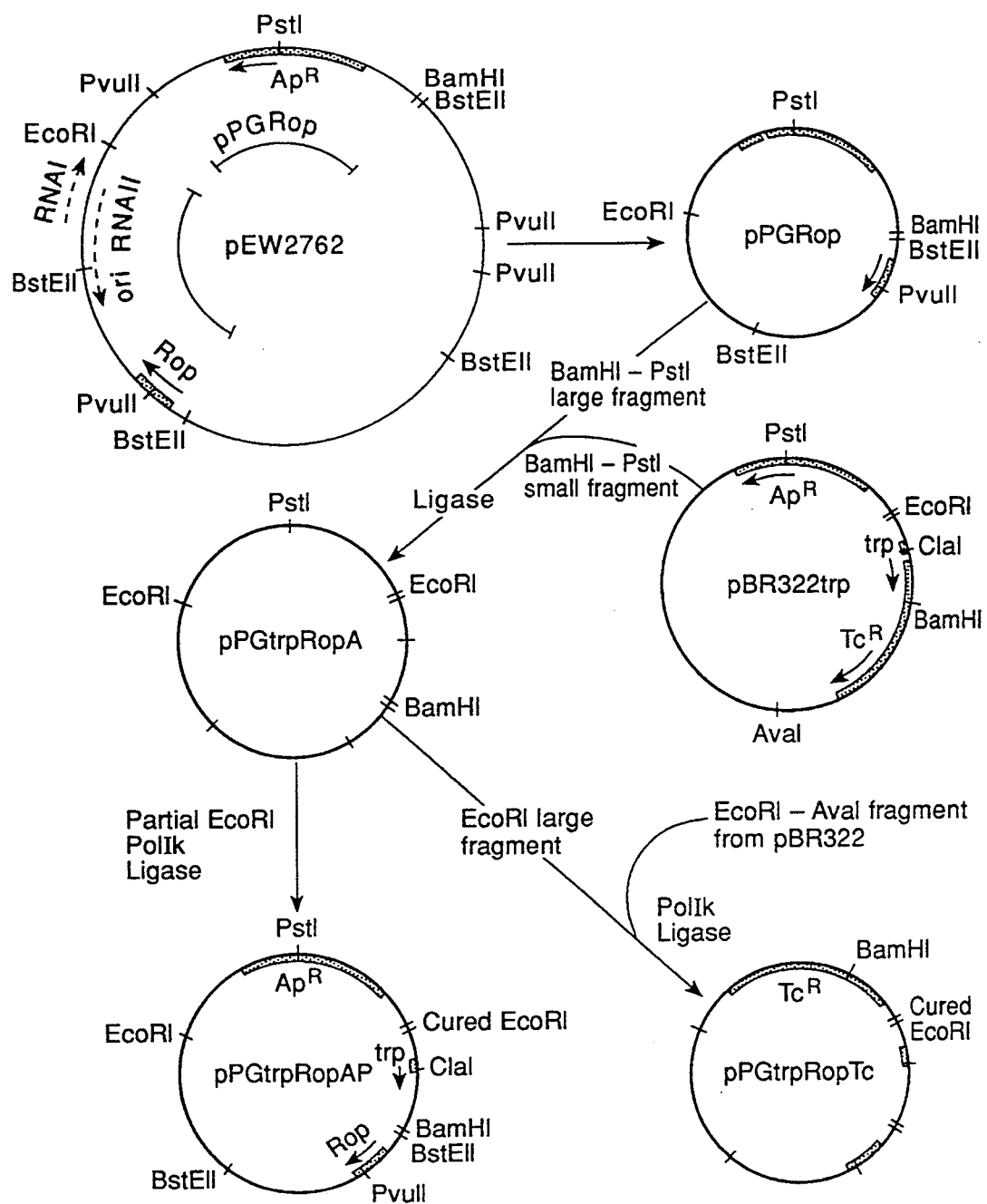
FIG. 1. Construction of expression vectors pPGtrpRopTc (suppressing plasmid) and pPGtrpRopAp (expression plasmid).

The present invention relates to a genetic expression system comprising two independently replicating genetic elements and additional genetic constituents. The independently replicating elements of this invention comprise any of the following which are presented only as examples and are not limiting of the scope of this invention: variants of DNA or RNA virus genomes including proviruses, nonviral genomes that are typically encoded in circular DNA molecules including plasmids, and complex genomes with both viral and nonviral origins including, for instance, "phagemids" or "cosmids".

The first independently replicating element exhibits a runaway-replication phenotype that is suppressed by a diffusible factor. For systems comprising bacterial plasmids, for instance, an exemplary plasmid exhibiting this suppressible phenotype comprises a complex of several mutations affecting different aspects of the regulation of plasmid replication. In particular, it has been found in an E. coli plasmid that when mutations in the RNA primer for DNA replication, which produce a conditional runaway-replication phenotype, are combined with mutations in a plasmid protein (Rop) that modulates plasmid replication by interacting with that RNA primer, a runaway-replication phenotype results. This phenotype is manifest even at a low temperature at which the temperature-dependent runaway phenotype of the RNA primer mutations alone is not manifest. This runaway phenotype is not exhibited, however, by plasmids bearing only mutations that eliminate the Rop regulatory function. Although the following theory of operation may be helpful for understanding of this invention, it is not provided to limit the scope of the present invention. According to the inventors, it is suspected that in the absence of the stabilizing influence of Rop protein on the interaction of the RNA primer (RNA II) with regulatory RNA I, even at a low temperature the ts mutations in the RNA primer cause sufficient structural instability to preclude effective interaction of RNA II with RNA I.

Regardless of mechanistic foundation, a particularly important aspect of the runaway-replication phenotype for this embodiment of this invention is that this phenotype is suppressible by Rop protein produced by another plasmid that is co-resident with the first plasmid in the same cell. In contrast, the primer mutations in this particular embodiment are not suppressible by a diffusible product; moreover, mutations eliminating only Rop protein function do not by themselves exhibit a runaway-replication phenotype.

There is a general test for identification of independently replicating elements that are suitable for use as the first independently replicating element in the present invention, that is, independently replicating elements that exhibit a runaway-replication phenotype that is suppressed by a diffusible factor. This test comprises application of the previously cited strategy that has been used by several investigators to identify those runaway-replication mutations in plasmids that affect a diffusible factor (Shepard et al., 1979, Cell 18, 267–275; Twigg and Sherrat, 1980, Nature 283, 216–218). According to the practice of this aspect of the present invention, it is believed that one of ordinary skill in the art is enabled to identify mutations exhibiting a suitable suppressible runaway-replication phenotype by growing cells containing both unmodified and mutagenized forms of, for instance, a given plasmid with different selectable markers, selecting for cells bearing only the marker of the mutant plasmids, and observing which mutant plasmids subsequently kill the host due to overproduction of plasmid DNA.

In another specific embodiment of the present invention, the first independently replicating element comprises an element originating at least in part from a viral genome including, for example, a bacteriophage λ prophage. According to this embodiment, the diffusible factor that suppresses the runaway-replication comprises the λ repressor protein (i.e., the product of the λ $C_I$ gene), the runaway-replication comprises the usual process of replication of λ DNA that is induced in the absence of the repressor; moreover, a promoter that is negatively regulated by this same λ repressor comprises the promoter for expression of a gene inserted into the first element.

The first independently replicating element of this invention further includes a site for insertion of a gene to be expressed. Although this gene comprises various regulatory sequences as well as sequences encoding amino acids of the desired protein or peptide product, it will ordinarily be advantageous to insert only those sequences encoding desired amino acids and one or more translation termination codons at the 3' end of those amino acid coding sequences.

The site for insertion of the gene to be expressed is located in the first element so that expression of the inserted gene is under the control of a negatively regulated promoter. Negatively regulated promoters suitable for this aspect of this invention comprise promoters that are inducible by removal of a repressor that inhibits transcription initiation at the promoter by binding to it. In other words, inhibition of transcription initiation at promoters suitable for this aspect of the present invention must be able to be overcome by "titration" with excess promoter-related repressor binding sites consequent to runaway replication of the first independently replicating element. Such promoters that are known to provide high level expression of several genes may be advantageously employed in the present invention. Further, although promoter-repressor combinations classically comprise a protein repressor, other types of novel repressors, ones comprising nucleotides complementary to promoter sequences, for example, would also be suitable for the practice of the instant invention, provided such novel repressors could be produced by expression of one or more genes. The requirements for locating a gene with respect to the promoter so that it is under the control of the promoter are extensively described in the literature for a variety of known promoters that are suitable for practice of the present invention.

In addition, the first independently replicating element (as well as the second independently replicating element) also includes a selectable marker for maintenance of the element in a host cell. Many antibiotic resistance genes are known to be suitable for this purpose in cases where the first element comprises various plasmids. Other markers, including nutritional requirement genes, may also be employed by those skilled in the art, for maintenance in cultures of the independently replicating element of this invention, although it will be readily recognized that convenient and economical selection agents may be advantageously employed, particularly for the first element, when large cultures are to be grown.

The genetic expression system of the present invention further comprises a second independently replicating element that includes a gene that expresses the diffusible factor that suppresses the runaway-replication phenotype in the first independently replicating element. In this usage, of course, it will be understood that the phrase "a gene that expresses the diffusible factor" is meant to convey the fact that, under the conditions for growing cells containing both the first and second elements, the gene of the second element that expresses the diffusible factor does so at a level sufficient to suppress the runaway-replication phenotype of the first element.

The second independently replicating element also includes a selectable marker for maintenance of the second element in the host cell, co-resident with the first element, that is different from the marker of the first element.

Finally, the expression system of this invention further comprises a gene that expresses a repressor of the negatively regulated promoter for gene expression, this repressor gene being located on a genome other than the first element, for instance, on the host cell genome. The phrase "a gene that expresses a repressor of the negatively regulated gene expression promoter" as used herein is meant to impart analogous meaning to the corresponding phrase concerning "a gene that expresses the diffusible factor" (see above). Further, it should be appreciated that this repressor gene may be located on any genome in a cell wherein the two plasmids are co-residing, including on the second plasmid, provided only that the genome on which the repressor gene is located is not amplified with the first element when its runaway-replication phenotype is expressed.

In the practice of this aspect of the present invention, the level of the first element which produces induction of transcription at the negatively regulated promoter may be controlled advantageously for the expression of various genes. According to the this practice, the level of repressor for the negatively regulated promoter may be adjusted in cells carrying both independently replicating elements, for example, by selection of a promoter for the repressor gene that causes production of more or less repressor from any given number of copies of the repressor gene. Other means for adjusting the level of repressor will be apparent to one of ordinary skill in the art of gene expression.

In a major embodiment of one particular aspect of the present invention, the location in the first independently replicating element of the site for insertion of a gene to be expressed is within the gene for the diffusible factor that suppresses the runaway-replication phenotype of the first element. Accordingly, in this case, the system is operated in part by fusing the gene encoding the desired protein product to the gene to be expressed. This fusion step serves to accomplish two distinct objectives: it inactivates the diffusible factor that suppresses the runaway-replication phenotype, thereby cause the first element to exhibit this suppressible runaway-replication phenotype of this invention; and more important, this fusion step also simultaneously renders the desired product in an advantageous form for isolation in high yields, to wit, in an insoluble fusion protein that contains the desired product and additional amino acids of the diffusible factor that suppresses runaway replication.

Further, this gene insertion site is selected to provide insertion of the gene to be expressed in the translational reading frame of the diffusible factor. In a most preferred embodiment, the diffusible factor that suppresses the runaway-replication phenotype is a plasmid protein that modulates inhibition of plasmid replication by interacting with the RNA primer for plasmid replication. The product of the rop gene of *E. coli* exemplifies such a most preferred diffusible factor. In this most preferred embodiment, the gene insertion site is under control of the trp promoter and, further, is located with the rop gene and, still further, is selected to provide an insoluble fusion protein that contains the product of gene to be expressed fused to additional amino acids of the Rop protein.

The first plasmid in this most preferred embodiment of this aspect of the invention is exemplified in *E. coli* by either of the two plasmids, pPGtrpRopAp or pPGtrpRopTc, further comprising a gene to be expressed inserted in the rop gene, while the second plasmid is typified by the other of the two plasmids, pPGtrpRopAp or pPGtrpRopTc, wherein the rop gene is intact.

The steps involved in the construction of these two particular plasmids, which in the absence of an inserted gene to be expressed overproduce the intact Rop protein, are detailed in FIG. 1 and Example 1, below. The 7.3 kb plasmid, pEW2762 (Wong et al., 1982, Proc. Natl. Acad. Sci. USA 79, 3570–3574), was the source of the Cop$^{ts}$ phenotype of both Rop protein overproducers. This plasmid contains two mutations in stem-loop IV of the primer transcript, or RNA II, that cause elevated copy number when cells harboring the plasmid are grown at 42 C.; the sequence changes involved in these mutations have been published (Wong et al., 1982, Proc. Natl. Acad. Sci. USA 79, 3570–3574; Wong and Polisky, 1985, Cell 42, 959–966). Accordingly, these mutations can be introduced into any plasmid comprising an RNA primer substantially homologous with that of pEW2762 using a short piece of synthetic DNA encoding these mutations, by methods that are well known in the art of genetic engineering. Thus, it is believed that one of average skill in the art of genetic engineering, without undue experimentation, can introduce the Cop$^{ts}$ phenotype of pEW2762 into another plasmid to provide an appropriate starting plasmid for making a first plasmid of the most preferred application embodiment of the present invention.

Overproduction of the Rop protein was first noticed when the trp promoter was cloned upstream from the rop gene and promoter which were located on pEW2762. To eliminate nonessential DNA and reduce multiple restriction sites a smaller version of pEW2762 was made (pPGRop) which contained a single PvuII site in the rop-coding sequence. The ori and copynumber control elements of pPGRop were combined with the trp promoter elements of pBR322trp to produce pPGtrpRopA. This combination of fragments placed the trp promoter about 500 bp upstream from a location where the rop promoter and subsequent coding sequence are believed to begin.

It should be noted here that although the presently most preferred embodiment of the first plasmid of this invention is thought to comprise the normal promoter of the rop gene, this fact has not been directly ascertained by DNA sequencing. There being no indication to the contrary in the art or in data obtained with this invention, and in the face of substantial theory in support of the contention that there is no obvious requirement for the rop gene promoter in the practice of this invention, therefore it is believed that the present invention does not, in fact, require the rop gene promoter or its analog in a first plasmid of this invention.

The plasmid pPGtrpRopAp (4.1 kb) was the vector used for all gene fusion experiments. It contains a single PvuII site, confers ampicillin (Ap) resistance, and displays runaway plasmid replication when grown at temperatures above 37 C. The plasmid pPGtrpRopTc (3.9 kb) confers tetracycline (Tc) resistance and has the same temperature-dependent copy number as pPGtrpRopAp. In this most preferred embodiment of this invention, the Tc$^R$ plasmid exemplifies the second plasmid that supplies Rop activity to cells transformed with lethal runaway copy number rop fusion plasmids.

Figure 2:
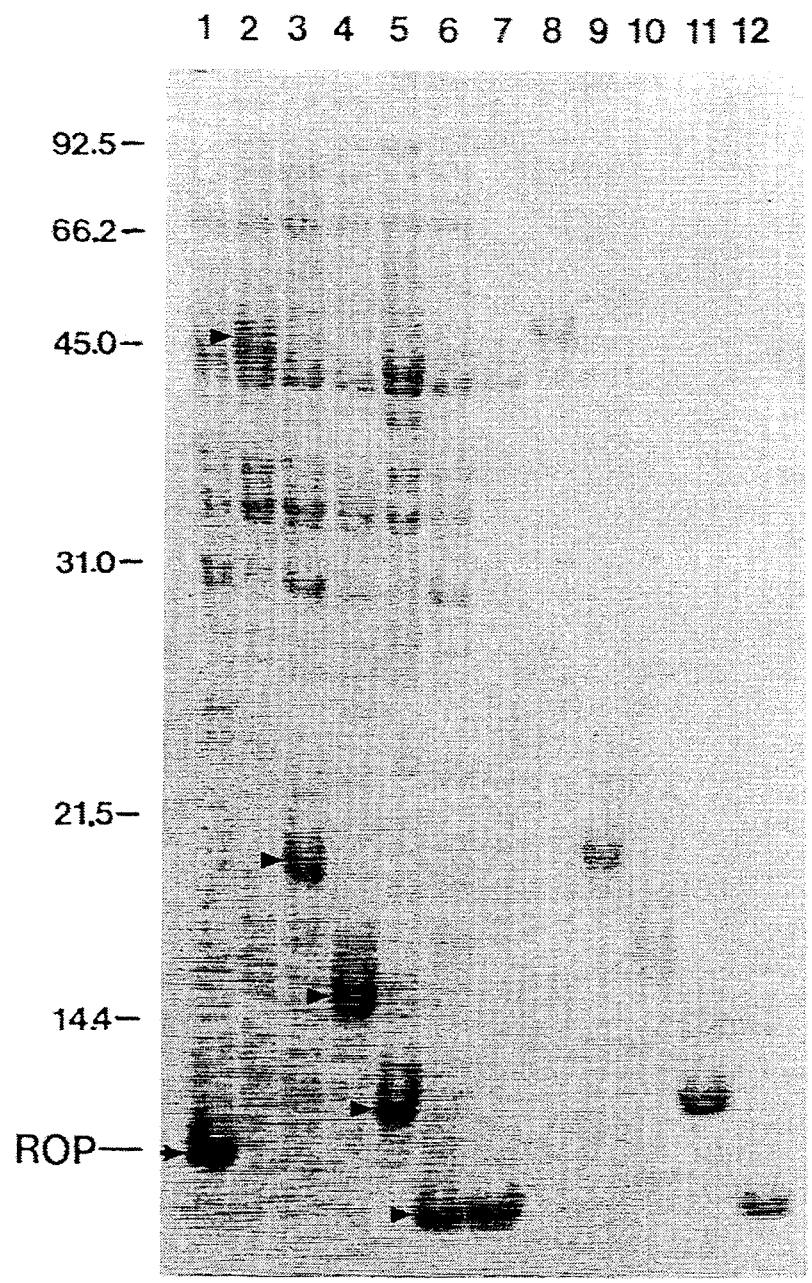
FIG. 2. Illustration of high level protein production by electrophoretic analysis of overproduced proteins in a 0.1% SDS/16% polyacrylamide gel.

In the absence of any inserted gene, the exemplary expression plasmid alone (i.e., pPGtrpRopAp in HB101 *E. coli* cells) produces high levels of the intact Rop protein in a two-step process involving first thermal induction of runaway plasmid replication and then chemical induction of Rop expression under the control of the trp promoter, as described in Example 2, and illustrated by the results in FIG. 2. This single-plasmid system is able to produce the Rop protein at 240 mg/liter. In addition to the high cellular concentration, the system also affords isolation of the bacterial protein at 90–95% yield and 80% purity by a simple periplasmic extraction.

Attempts were made to harness the high level expression of the Rop protein exhibited by the single expression plasmid for expression of other polypeptides, by inserting genes into the Rop coding sequence in such a way that production under the trp promoter of fusion proteins containing amino acids encoded by both the rop gene and the inserted gene was anticipated. The rop gene contains a PvuII restriction site that cleaves the coding sequence after the 2nd nucleotide of codon No. 51 (AG/C), 12 amino acids (aa) from the C terminus. DNA fragments can be blunt-end ligated at this point to encode rop gene fusion proteins beginning at aa 52. The aa 51 is maintained as a Ser or converted to an Arg depending upon the first nucleotide of the ligated fragment. This is described in Example 3 and illustrated in FIG. 3 which shows the DNA and amino acid sequences around the PvuII site.

The model fusion plasmid comprising pPGtrpRopAp and the 404-bp HpaII fragment from pBR322, which is designated herein by abbreviated nomenclature as prop-404, was constructed to serve as the initial test of the single plasmid fusion system. This construct re-established the Ser codon at aa 51 and added an additional 51 aa before encountering a stop codon. The construct pRop-MT consists of a ligation of a pUC9 fragment containing the entire Chinese hamster metallothionein (MT) gene. The fusion Rop-MT (opp) is the opposite orientation of the MT gene in the pUC9 fragment. pRop-Tat contains a fusion with the entire coding sequence of the HIV trans-activator, or tat gene. pRop-HSV-38K encodes a fusion protein with the HSV (herpes simplex virus) type 2 38K protein.

Despite repeated attempts, no fusion transformants could be obtained when HB101 was transformed with ligation reactions that interrupted the rop gene in the isolated expression plasmid pPGtrpRopAp. Cells harboring prop-404 produced colonies at 30 C. on Ap plates, but colony inoculations in YT medium yielded cultures that produced barely detectable growth after 48 hours at 30 C. No colonies were obtained with either MT ligation. The same results were obtained when the fragments were ligated to pPGRop. Since this vector does not contain the trp promoter, protein overproduction was probably not the reason for growth inhibition.

Accordingly, the vector pPGtrpRopTc was constructed to see if the presumed runaway replication of the expression plasmid could be suppressed by supplying functional Rop protein activity to cells harboring these fusion plasmids. When the host harboring this second plasmid, i.e., HB101[pPGtrpRopTc], was transformed with the fusion ligation reactions and plated on YT agar containing both Ap and Tc for selection of both plasmids, colonies were obtained after 18–24 hr at 30 C. Plasmid DNA extracted from cultures of doubly transformed cells (grown in both antibiotics at 30 C.) showed both plasmid species in about equal amounts and at normal levels (approximately 500 ng/ml). Small amounts of the fusion plasmids were isolated on agarose gels in order to eliminate the helper plasmid. No transformants could be obtained when using this DNA to transform HB101. This result confirmed the lethality of these constructs and illustrated the necessity of using the second plasmid for trans suppression of the runaway-replication phenotype of the expression plasmid.

It has been found that simply diluting doubly transformed cells in YT medium (30 C.) containing only Ap results in the gradual loss of the (second) suppressor plasmid. Consequently, it appears that the trp operator is gradually induced via repressor titration as fusion plasmid DNA levels increase, and fusion proteins accumulate at high levels.

Example 4 describes the growth and induction of doubly transformed cells harboring pRop-Mt, prop-404, and pRop-MT(opp), and other fusions, while FIG. 2 shows the results these expression tests. To confirm the general applicability of this protein production system, two additional constructs were undertaken. Fusions were made with the HIV Tat protein and the HSV type 2 38K protein. The Tat protein was chosen because of its importance in the study of the HIV disease process (Aldovini et al., 1986, Proc. Natl. Acad. Sci. USA 83, 6672–6676; Muesing et al., 1987, Cell 48, 691–701) and because of its similarities to the MTs (Frankel et al., 1988, Science 240, 70–73). The HSV protein was chosen because of its sequence homology to the small subunit of ribonucleotide reductase of several pathogenic viruses (Gibson et al., 1984, Nucleic Acids Res. 12, 5087–5099; Swain and Galloway, 1986, J. Virol. 57, 802–808). These additional tests also served to determine the effects of protein size on the high level protein production in this most preferred embodiment of the present invention. As shown in FIG. 2, the accumulations of both the Tat and HSV fusion proteins were about 20% of the total bacterial protein.

Purification of fusions was carried out as detailed in Example 5 in order to confirm their identity by peptide mapping, because antibodies to most of the proteins were not readily available. To date seven fusion proteins have been produced using this system. All of the proteins have accumulated as surprisingly insoluble aggregates and have been easy to obtain free of other contaminating bacterial proteins by simple centrifugation of disrupted cells. The yields of the purified fusion proteins range from 100 g/ml to 170 g/ml. These observations illustrate that the bacterial expression system of the present invention has wide applicability that offers a novel means for production of a number of clinically important proteins in a form that can be purified easily at high yield and low cost.

Figure 4:
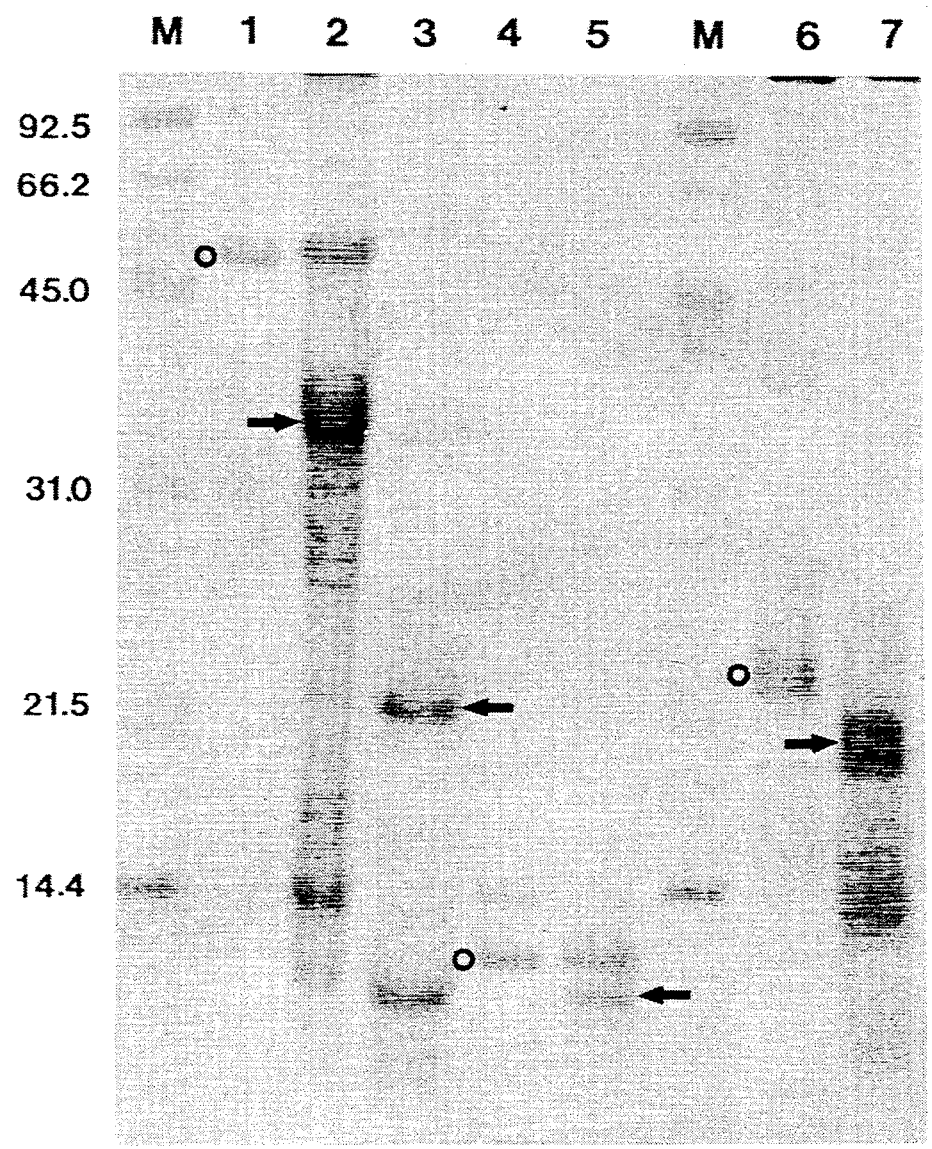
FIG. 4. Chemical cleavage of partially purified fusion proteins.

Five fusion proteins produced by this expression system were identified by their fragmentation patterns after cleavage at Met with CNBr, and/or at acid labile Asp-Pro bonds, as presented in Example 6. FIG. 4 shows the results of some of these reactions.

Figure 5A:
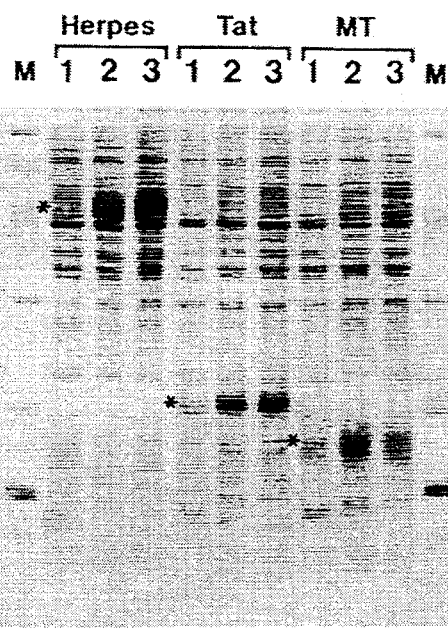
FIG. 5. Analysis of fusion protein induction and accumulation.
Figure 5B:
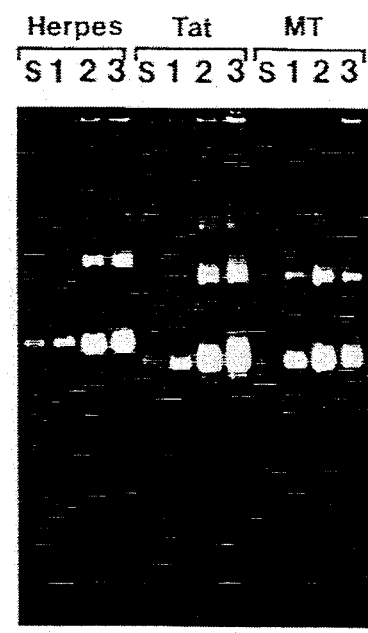

All five fusion constructs produced proteins at consistently high levels if the starter cultures containing both antibiotics were diluted at least 5000-fold in medium containing only the selection agent for the expression plasmid. This was the minimum dilution necessary to achieve high-level plasmid amplification and concomitant protein production. FIG. 5 illustrates the strong correlation between fusion protein accumulation (5A) and plasmid DNA amplification (5B). Plasmid DNA levels reach 20–30 $\mu$g/ml of growth medium after 36 hr.

The factors that cause some proteins to accumulate in bacteria as insoluble aggregates are poorly understood, but the factor that most of the reported proteins have in common is high cellular concentration (Marston, 1986, Biochem. J. 240, 1–12). To determine if a soluble protein component existed early in induction growth at lower protein concentrations, fusion protein samples were separated into soluble and insoluble protein fractions at the 24-h and 48-h time points. As described in Example 7 and illustrated in FIG. 5, all the tested Rop fusions appear to accumulate as insoluble aggregates early in induction growth and do not seem to form simply because of high cellular concentrations.

These experiments illustrate the need to incubate cultures longer than 24 hr to achieve maximum levels of accumulation even though the cultures are approaching stationary phase by this time. This requirement is particularly apparent in the pRop-HSV 38K induction, since little fusion protein accumulates at 24 hr. By simply varying the dilution of the starter culture, the expression systems for each of the five fusions could be fine-tuned to yield maximum intracellular fusion accumulation and maximum culture density. According to the practice of this aspect of the invention, protein yields of between 100 and 170 $\mu$g/ml after 40 hr of incubation at 30 C. have been achieved consistently for all tested genes.

Bacterial expression systems for a large number of eukaryotic proteins that accumulate as soluble protein or insoluble aggregates have been described (Marston, 1986, Biochem. J. 240, 1–12). As noted under background, several systems combined the features of the thermoinducible runaway plasmid pKN402 (Uhlin et al., 1979, Gene 6, 91–106) and efficient promoters to produce high-level expression in bacteria. Few of these systems, however, consistently produce proteins as insoluble aggregates as predictably as this runaway-replication rop fusion system of the present invention. In addition, systems utilizing pKN402 sometimes suffer from problems with high temperature runaway-replication: plasmid instability (loss of plasmid or plasmid deletions) and host growth impairment (Uhlin et al., 1979, Gene 6, 91–106; Remaut et al., 1983, Gene 22, 103–113). After several inductions with more than ten different constructs, no plasmid deletions, growth impairment, or premature shutdown of protein synthesis has been detected in the most preferred embodiment of this system in E. coli.

Expression systems consisting of fusions with the trpE gene (Marston, 1986, Biochem. J. 240, 1–12; Hoffman et al., 1987, Cell 51, 919–928; Muesing et al., 1987, supra) or lacZ gene (Guo et al., 1984, Gene 29, 251–254; Marston, 1986, supra) may produce insoluble fusion proteins at levels comparable to the system of the present invention. However, these systems typically utilize 188 to 320 aa of the TrpE polypeptide or, alternatively, approximately 550 aa of β-galactosidase, to produce fusion proteins with yields as high as 200 μg/ml. In such large fusions, however, the desired polypeptide may be substantially shorter than its fusion partner and, therefore, constitute only a fraction of the total fusion peptide mass. In contrast, the Rop moiety in fusions of the present system are small, for example, less than 55 aa, and thus the yields of the actual sequence of interest (when yields of the purified fusion proteins range from 100 μg/ml to 170 μg/ml) are significantly higher than in the other fusion expression systems, especially in the case of small proteins like MT and Tat.

The presently preferred embodiment of the expression system we have developed in E. coli produces insoluble proteins at consistently high yields, on a scale ranging from 5 ml to at least several liters, without temperature shifts, inducers, or specialized growth medium. The cultures do not require high aeration; therefore, fairly large volumes can be cultivated without requiring fermentation equipment. Due to the simplicity of the dilution step used to initiate automatic induction of gene amplification and expression, a step which is inherent in the process of expanding cultures for protein production on any scale, there appear to be no obstacles to prevent one of average skill in the art of fermentation, without undue experimentation, from application of the present invention to protein production on essentially any scale for which culture methods are known.

An additional advantage of the embodiment of this system employing a Rop fusion is that the Rop moiety does not mask or interfere with the antigenic determinants of tested proteins. The Spec protein (Muesing, et al., 1984) is one example that has been tested for antigenicity in Rop fusions. Therefore, partially purified Rop fusion proteins can be used to produce antibodies in the same manner as TrpE and β-galactosidase fusions. If necessary, the Rop portion of the protein molecule can be removed by chemical methods. Purification of the fragmented proteins is simplified because the cleavage products of Rop are quite small. In conclusion, the presently preferred embodiment of the expression system of this invention is highly stable, and yields of each fusion can be optimized simply by varying the dilution of an overnight culture. Accordingly, this system may be especially valuable in the production of small proteins and polypeptides that are frequently degraded in bacteria.

EXAMPLE 1

Construction of plasmid precursors to the preferred expression plasmids.

Throughout the present example and the others below, the following materials and methods were used as needed. Restriction enzymes, T4, DNA ligase, polynucleotide kinase, and polk were purchased from New England Biolabs. Restriction enzyme digestions, ligations, and polymerase reactions were performed as recommended by suppliers or as described in Maniatis et al., 1982, A Laboratory Manual, Cold Spring Harbor Laboratory, Cold Spring Harbor, N.Y.

Protein quantitation and amino acid sequencing were performed as follows. 0.1% SDS/15.5% polyacrylamide gels (Laemmli, 1970, Nature 227, 680–685) were stained (0.2% Coomassie Brilliant Blue, 50% methanol, 12% glacial acetic acid), destained, and scanned using a Kontes Model 800 Fiber Optic Scanner; peaks were quantitated using a Hewlett Packard 3390 A Reporting Integrator. The Rop protein was sequenced by Applied Biosystems (Foster City, Calif.) after purification of the protein by hydroxyapatite chromatography. Fragments obtained from chemical cleavage reactions (see below) were separated on the same gels, electroblotted, and sequenced as described (Hsieh et al., 1988, Anal. Biochem. 170, 1–8).

The following bacterial strains and plasmids were also used. Escherichia coli K-12, strain HB 101 (pro, leu, thi, lacY, hsdR, endA, recA, rpsL20, ara-14, galK2, xyr-5, mtl-1, supE44) was used in all transformations. The plasmid pEW2762 was obtained from Drs. E. Wong and B. Polisky. The plasmid pPS21, which was the source of the E. coli trp gene promoter was obtained from Dr. C. Yanofsky of Stanford University; however, plasmids comprising this same promoter are available from commercial sources (e.g., Pharmacia). Plasmid pCV-1, the source of the tat gene, was obtained from Dr. R. Gallo of the National Cancer Institute. pCHMT1, comprising the MT-1 metallothionein gene, was obtained from Dr. C. E. Hilderbrand. Dr. Laura Aurelian supplied the plasmid pJW7, the source of the HSV 38K gene.

The plasmid pPS21 is a pBR322 derivative containing the trp promoter and trpE gene. A 0.5-kb HinfI fragment containing the trp promoter and leader gene was isolated on a 6% polyacrylamide gel. This fragment was subjected to a partial TaqI digestion, and the resultant fragments were ligated into the ClaI site of pBR322. pBR322trp has trp promoter transcription in the direction of the $Tc^R$ gene (Sutcliffe, 1979).

pEW2762 was digested with BstEII and a 1.1-kb fragment (containing the rop gene and ori) and 3.0-kb fragment (containing the regions coding for RNA I, RNA II, and $Ap^R$ were isolated and ligated to form a 4.1-kb plasmid (pEW2762dl) containing two BstEII and two PvuII sites. Cleavage of this plasmid with PvuII+EcoRI followed by blunt-end ligation (EcoRI ends made blunt with PolIk and dNTPs) of the two larger fragments yielded pPGRop (3.7-kb). pPGRop was digested with PstI+BamHI, and the larger fragment (2.8-kb) was ligated to the smaller PstI-BamHI fragment (1.4-kb) of pBR322trp (construction described above) to produce pPGtrpRopA. The expression vector pPGtrpRopAp was produced by elimination of the EcoRI site near the trp promoter, to facilitate future constructions. The plasmid pPGtrpRopTc is identical to pPGtrpRopAp except that the EcoRI-AvaI fragment of pBR322 that confers $Tc^R$ was ligated between the EcoRI sites of pPGtrpRopA. [Note that this is not identical to the plasmid pPGtrpRopAp, but rather it is an intermediate in formation of that latter plasmid.]

In FIG. 1, heavy lines represent the coding regions for Rop, $Ap^R$ and $Tc^R$. The small box at the ClaI site in pBR322trp represents the trp promoter sequence. Restriction sites important to plasmid construction are shown; some sites are not labeled but are represented by a bar. Arrows denote the direction of transcription of the various genes. Dashed arrows denote the direction of transcription of RNA I and RNA II; ori, the origin of DNA replication.

EXAMPLE 2

Rop protein overproduction by an expression vector in E. coli.

The following methods for transformations and cultivation of cells transformed with expression plasmids were used through this and the following examples as needed.

HB101 was made competent for transformation with pPGtrpRopAp and pPGtrpRopTc by the standard CaCl$_2$ procedure (Maniatis et al., 1982, supra), except that cells were cultivated at 30 C. after heat-shock treatment. Ap and Tc were used at concentrations of 100 µg/ml and 10 µg/ml, respectively. YT medium (Miller, 1972, Experiments in Molecular Genetics, Cold Spring Harbor Laboratory, Cold Spring Harbor, N.Y.) consisted of 1% tryptone, 0.5% yeast extract, 0.5% NaCl and 0.1% glucose.

The host HB101[pPGtrpRopTc] is HB101 transformed with the vector pPGtrpRopTc, the suppressor plasmid which was used for the isolation of plasmids containing fragments inserted into the PvuII site of pPGtrpRopAp. A 100-fold dilution of fresh overnight culture of HB101[pPGtrpRopTc] (grown at 30 C. in 10 µg Tc/ml) was made in YT medium (5 µg Tc/ml), grown to mid-log phase, made competent, and transformed in the same manner as HB101. After the heat shock the cells were diluted with 100 volumes of YT medium and incubated at 30 C. for 30 min; Tc was added to a concentration of 7 µg/ml. After an additional 2 hr of incubation, Ap was added to a concentration of 100 µg/ml, and incubation was continued until saturation was achieved. After appropriate dilutions were made, cells were plated on YT plates (100 µg/ml Ap, 7 µg/ml Tc) and incubated at 30 C. to obtain individual colonies. Colonies were inoculated in 2 ml YT medium containing the same antibiotics and the DNA from these doubly transformed cells was extracted (Birnboim and Doly, 1979) and analyzed to determine the structure. Doubly transformed cells were stored in glycerol at −20 C. and used to make fresh starter cultures for fusion protein production.

Maximum production of Rop protein is achieved by first growing cultures of HB101[pPGtrpRopAp] overnight at 39–40 C. in YT medium. Under these conditions the trp promoter is partially repressed an cellular plasmid DNA levels reach 15–20 µg/ml. After centrifugation and washing, the cells are resuspended in M9 medium containing the nonmetabolizable inducer of the trp repressor, 3β-indolyacrylic acid, and incubated at 30 C. This second incubation was under conditions that favored total derepression of the trp promoter but did not favor runaway plasmid replication.

FIG. 2 illustrates the results of this two step procedure when applied to cells harboring pPGtrpRopAp. After plasmid amplification at 39 C. and protein induction at 30 C., Rop protein accumulated to 31% of the bacterial protein shown in lane 1. Even though Rop is not post-translationally modified, more than 85% of the Rop protein was obtained by a simple periplasmic extraction of the pelleted cells. The Rop protein obtained in the periplasmic extract (lane 7) was determined to be 81% pure with less than 5% of the protein remaining in the cell pellet (not shown) after a single extraction.

Lane 1 contains cells from Rop overproducer HB101 [pPGtrpRopAp] after induction in M9 medium (proteins from 15 µl of culture). A 1000-fold dilution of an overnight culture (grown at 30 C. in YT medium containing 100 µg Ap/ml) was made in 1 liter YT medium (300 µg Ap/ml) and incubated at 39 C. for 18 hr. Cells were pelleted and resuspended in 1 liter of M9 medium (Miller, 1972) which was supplemented with 0.4% casamino acids, 50 µg 3β-indolylacrylic aid/ml, 300 µg Ap/ml, and induced for 18 hr at 30 C. After pelleting and washing, the cells were subjected to a periplasmic extraction as described by Neu and Heppel (1965). Lane 7 represents the periplasmic extracted proteins form the same number of cells as lane 1.

An interesting feature of this protein production system is the Rop is practically the only protein labeled if the isotope is added after overnight induction in M9 medium. This selection labeling was quite useful because the entire labeling reaction could be used as a radioactive marker in large scale purifications or other manipulations.

The weight of cells processed from this induction was 7.8 g or about 1 liter of culture at an OD$_{660}$ of 4.4. Periplasmic extracts shown in lane 7 gave values of 190 g/ml using the Bio-Rad protein assay (standard No. 2) and 300 µg/ml using gravimetric methods. Since Rop constituted about 80% of the extract, the yields were 150 µg/ml and 240 µg/ml, respectively. Quantitative sequencing data showed better correlation to the 240 µg/ml estimate, suggesting that Bio-Rad Standard No. 1 is a more appropriate standard for the quantitation of purified Rop samples.

By way of comparison of the present expression plasmid with others, systems that have been used to overproduce Rop protein, as described in the literature, may be considered. Some of these plasmids utilized the $\lambda P_L$ promoter to produce Rop at purified yields of 30–60 mg/100 g of cells (Lacatena et al., 1984, Cell 37, 1009–1014; Tomizawa and Som, 1984, Cell 38, 871–878). Yields of 2–3 g/ml have been reported using the vector pMAM7 (Muesing et al., 1984, Gene 31, 155–164; Dooley and Polisky, 1987, Plasmid 18, 24–34). These expression systems required several steps to purify the protein. The present system with the expression plasmid alone produced Rop protein at levels of 150–250 µg/ml of culture (19–31 mg/g of packed cells) with a one-step purification. This system is therefore a powerful method of producing this functionally important protein for further research.

EXAMPLE 3

Construction of rop-fusion plasmids.

In FIG. 3, the last 14 aa of the Rop protein (Cesareni et al, 1982, Nat. Acad. Sci. USA 79, 6313–6317) and the 11-aa region surrounding the points of fusion are shown. The underlined portions of the aa sequences denote the extent of uninterrupted Rop sequence, and the arrows above the nucleotide sequences mark the points of ligation. The numbers beneath the fusion designations denote the number of aa in protein and the calculated size in kDa based upon the reading frame established at the point of ligation.

The fusion prop-404 was constructed by ligating the 404-bp HpaII fragment from pBR322. The fragment was made blunt-ended by filling in the CC overhang, and was then ligated to PvuII-digested, phosphatase-treated pPGtrpRopAp.

pRop-MT contains a fusion with the Chinese hamster MT-1 gene. The starting material for this construction was a 288-bp fragment produced by an AvaII+HinfI digestion of the plasmid pCHMTI (Griffith et al., 1983, Nucleic Acids Rec. 11, 901–910). After ligating ClaI linkers the fragment was inserted into pUC9 (Vieira and Messing, 1983, Gene 19, 259–268) at the AccI site, and both orientations were obtained. The pUC9 clones were restricted with EcoRI+HindIII, and the resultant 326- bp fragments were filled-in and ligated to pPGtrpRopAp. Both the constructs (with the two different orientations of MT relative to transcription) produce a Ser-to-Arg mutation at aa 51 (recreating the pUC9 EcoRI site), and contain the pUC9 polylinker sequence encoding the six aa from aa 52 to aa 57. The pRop-MT plasmid encodes the entire MT protein beginning at aa 55 and ending at aa 118. The pRop-MT(opp) construct encodes a protein of 73 an (8.5 kDa), because double stop codons are encountered 22 aa from the fusion point.

To obtain the tat gene in a form suitable for fusing to the rop gene, pCV (Arya et al., 1985, Science 229, 69–73) was digested with BamHI+SalI to obtain a 356-bp fragment. Digestion of this fragment with Sau3A produced a 279-bp fragment that encoded the entire tat gene except for the first four aa, met-glu-pro-val. A synthetic adaptor with the sequence

5'-CTGCATGGAGCCAGTA
  GACGTACCTCGGTCATCTAG-3' was made that encoded cys-met-glu-pro-val and supplied aa 52 of Rop (cys) as well as the missing four aa of Tat. The unphosphorylated adapter was ligated to the 279-bp Sau3A fragment to form a 315-bp blunt end fragment which was phosphorylated, and ligated to the expression vector. The Mets at the following positions, aa 58 in pRop-MT, aa 53 in pRop-Tat, and aa 52 in pRop-HSV 38K, mark the beginning of the aa sequences of each of the respective native proteins.

The plasmid pJW7 contains the entire coding region of the Herpes 38K protein which was excised from the plasmid by digestion with NcoI+XbaI. The 1.0-kb fragment was isolated, filled in with PolIk and dNTPs, and ligated to the expression vector.

EXAMPLE 4

Production of fusion proteins using doubly transformed cells.

FIG. 2, lanes 4, 5 and 6 show the results of the growth and induction of doubly transformed cells harboring pRop-Mt, prop-404, and pRop-MT (opp), respectively. The prominent protein bands (arrows) show good agreement with the predicted mobilities ($M_r$s) for these proteins, and the average accumulation was 20% of the total bacterial protein after 40 hr of growth at 30 C. Rop-MT(opp) appears to be about the same size as the Rop protein in lane 7; however, its higher $M_r$ was obvious on peptide mapping gels (Jue and Doolittle, 1984).

FIG. 2, lanes 2 and 3 shows the result of the growth and induction of cells harboring pRop-HSV 38K and pRop-Tat, respectively. Prominent bands of the proper (arrows) are obvious in these lanes. Lanes 2–6 contain total SDS soluble protein (25–30 μl of culture) after induction for 40 h at 30 C. The inductions are arranged by decreasing $M_r$ of the fusion proteins, in the order Rop-HSV 38K, Rop-Tat, Rop-MT, Rop-404, and Rop-MT(opp). Induction growth was initiated by inoculating 1 μl of starter cultures in 50 ml YT medium (500 μg Ap/ml). After incubation for 40 h at 30 C., cells were pelleted, washed in 20 mM Tris (pH 7.8), lysozyme treated ($10^{10}$ cells/ml), sonicated, and insoluble fusion proteins recovered as described by Kaplan and Greenberg (1987). Lanes 8–12 contain GuHCl solubilized fusion proteins from the same number of cells as represented in lanes 2–6. Prior to electrophoresis the GuHCl was removed by dialysis against water. After lyophilization the proteins were dissolved in sample loading buffer (Laemmli, 1970, supra). All lanes contain proteins from $2\times10^7$ cells. The gel was stained as described above.

EXAMPLE 5

Fusion protein purification.

FIG. 2, lanes 8–12, shows the partially purified proteins after sonicated cells were fractionated by centrifugation and dissolved in 6M GuHCl. Densitometric scans of the gel indicated that the fusions accounted for 65% of the protein (75–80% with additional pellet washings) in the extracts, and the average yield was 105 μg/ml of growth medium. All the fusions could also be dissolved at concentrations of 5–10 mg/ml in 1–5M urea or 1% SDS. These protein stocks could be diluted to 1 M urea without precipitation of the protein. Solutions of Rop-Tat, free of denaturing agents, have been prepared in 10 mM Tris (pH 7.0), 1M NaCl. The Rop-Tat and Rop-Mt GuHCl solutions are dark amber in color, whereas the other extracts are colorless. This coloration may be due to the metal-binding properties of these two proteins.

EXAMPLE 6

Protein identification by chemical cleavage.

The dipeptide sequence Asp-Pro occurs twice in the Rop-HSV 38K protein (at aa 53–54 and 62–63), and cleavage at these positions should yield high $M_r$ fragments of about 36 kDa. In FIG. 4, the doublet in lane 2 (arrow) corresponds to these two fragments generated by this partial cleavage reaction. Cleavage of the full size fusion protein at Met (at six positions) should produce several fragments. The largest fragment, beginning at aa 53 (FIG. 3) is the 179-aa, 20.2-kDa band marked by the arrow in FIG. 4, lane 3. This protein was sequenced through the first 16 aa to confirm the identity of the fusion. The rest of the bands clustered below 10 kDa and were not resolved into individual bands on this gel.

Similar results were obtained when Rop-404 and Rop-Tat were cleaved at Met. The band in FIG. 4, lane 5 (arrow) corresponds to the 7.9-kDa fragment predicted by the nucleotide sequence. The band above the arrow corresponds to the 10.3-kDa fragment obtained from the cleavage of the residual lysozyme in the extract. Unfused Tat protein, obtained by cleavage at Met (aa 53 in Rop-Tat, FIG. 3), is shown in lane 7 (arrow). This fragment was also sequenced through the first 13 aa to confirm the identity of the protein. The structures of Rop-MT and Rop-MT (opp) were confirmed by their cleavage profile after treatment with CNBr. Specific methods for FIG. 4, for the indicated lanes: 1, Rop-HSV 38K GuHCl extract; 2, Rop-HSV 38K cleaved at Asp-Pro by incubation for 24 h in 50% formic acid/6M GuHCl at 40 C. (Szoka et al, 1986, DNA 5, 11–20); 3, Rop-HSV 38K cleaved at Met by incubation for 24 h in 70% formic acid/4 mg CNBr/ml at 24 C. (Jus and Doolittle, 1985, Biochemistry 24, 162–170); 4, Rop-404 GuHCl extract; 5, Rop-404 cleaved at Met under same conditions as lane 3; 6, Rop-Tat GuHCl extract; 7, Rop-Tat cleaved at Met under same conditions as lane 3.

All of the cleavage reactions were performed on GuHCl solubilized proteins after dialysis of the stocks against water and lyophilization. The dried proteins were dissolved in formic acid or formic acid/GuHCl at concentrations ranging from 1–5 mg/ml. The CNBr reactions were lyophilized, and portions were dissolved in sample loading buffer (Laemmli, 1970). Cleavage reactions at Asp-Pro were dialyzed (4 C.) against several changes of 20 mM Tris (pH 8.0) and finally against water. After lyophilization, portions were dissolved in sample loading buffer. The gel (0.1% SDS; 16% polyacrylamide) was stained as described above. The full size proteins (lanes 1,4,6) are marked by circles, and the cleavage products discussed are marked by arrows. For the complete amino acid sequence of these proteins see Gibson, et al (1984, Nucleic Acids Res. 12, 5087–5099; HSV 38K protein); Aldovini et al. (1986, supra; Tat protein); Griffith et al. (1983, supra; MT protein).

EXAMPLE 7

Fusion protein induction and accumulation.

Figure 5C:
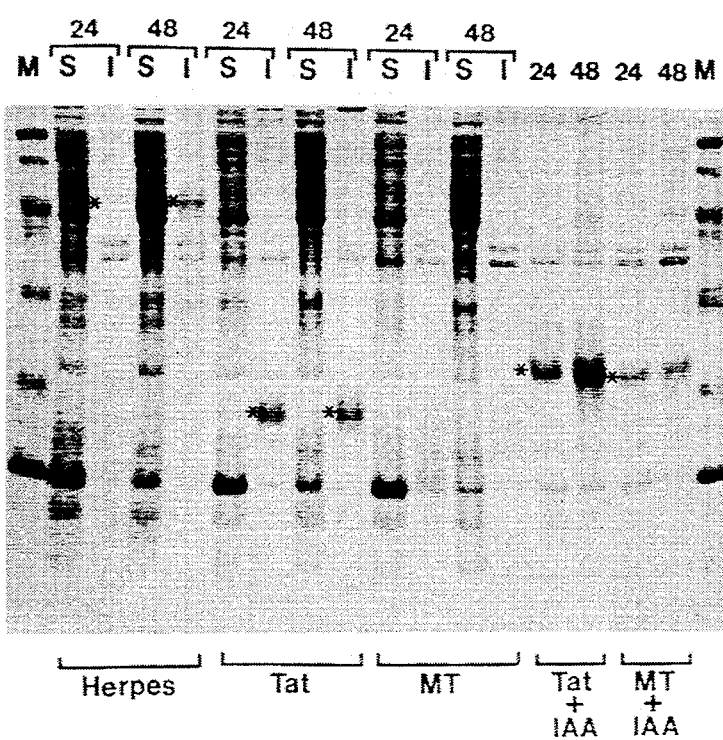

As can be seen in FIG. 5C, no soluble (S) fusions are evident in the Rop-Tat or Rop-MT samples at either time point even though cellular levels are lower at the 24 hr points. For accurate comparisons the insoluble fractions required carboxymethylation (IAA samples) to prevent precipitation (gel slot of Tat, 48 hr insoluble sample) or streaking (24 and 48 hr insoluble MT samples) during electrophoresis. The Rop-HSV 38K protein has very little accumulation at 24 hr; however, detectable amounts of the protein are present in the insoluble extract. At 48 hr 40–50% of this protein remained in the soluble fraction and was the only fusion that behaved in this manner. Additional details of methods for FIG. 5: (Panel A) 0.1% SDS/15.5% polyacrylamide gel of total SDS-soluble protein. Induction growth was initiated by inoculating 10 μl of starter culture (same growth conditions as in FIG. 2) in 50 ml of YT medium (500 μg Ap/ml). Flasks were shaken at 30 C. and 1 ml samples were removed at 24 hr (lanes 1), 36 hr (lanes 2), and 48 hr (lanes 3). Cells were pelleted and dissolved in sample loading buffer (Laemmli, 1970, supra). (Panel B) 1% agarose gel of supercoiled plasmid DNA. At the same time points as in FIG. 5A, 1 ml samples were removed and plasmids were extracted (Birnboim and Doly, 1979, Nucleic Acids Res. 7, 1513–1523). Each lane contains plasmid DNA from $5 \times 10^7$ cells (approximately 40 μl of culture in lanes marked 2 and 3). Lanes marked S contain DNA extracted from starter cultures. The last two lanes (next to MT samples) contain respectively 0.1 and 1.0 μg of expression plasmid DNA. Gel was stained with ethidium bromide (0.5 μg/ml). (Panel C) 0.1% SDS; 15.5% polyacrylamide gel of protein fractionation. At 24 and 48 h, portions of the cultures were removed, and cells were pelleted, washed, lysozyme treated, and sonicated (Kaplan and Greenberg, 1987, Proc. Natl. Acad. Sci. USA 84, 6639–6643). After the $100,000 \times g$ centrifugation, the soluble (S) supernatant proteins were concentrated by precipitation in 5 vols. of acetone, and dissolved in sample loading buffer. The insoluble pellet (I) was dissolved in sample loading buffer containing 5 M urea. IAA samples are those that were carboxymethylated by treatment with iodoacetic acid after complete reduction in dithiothreitol (Marks et al, 1987, Science 235, 1370–1373). All sample lanes of polyacrylamide gels (stained as described above) contain protein from $2 \times 10^7$ cells, or an average volume of 16 l of culture in the 36 and 48 h time points. Fusion proteins are marked by asterisks. Herpes, HSV protein.

For purposes of completing the background description and present disclosure, each of the published articles, patents and patent applications heretofore identified in this specification are hereby incorporated by reference into the specification.

The foregoing invention has been described in some detail for purposes of clarity and understanding. It will be obvious to one of ordinary skill in the art that various combinations in form and detail can be made without departing from the scope of this invention.

What is claimed is:

1. A genetic expression system comprising:
   a first independently replicating element which includes
      a site for insertion of a gene to be expressed wherein expression of said gene is under the control of a negatively regulated promoter, and
      a selectable marker for maintenance of said first independently replicating element in a host cell,
   wherein said first element exhibits a runaway-replication phenotype that is suppressed by a diffusible factor; and
   a second independently replicating element which includes
      a gene that expresses said diffusible factor that suppresses said runaway-replication phenotype of said first element, and
      a selectable marker for maintenance of said second element in said host cell that is different from said marker of said first element; and
      a gene that expresses a repressor of said negatively regulated promoter, said repressor gene being located on a genome other than said first element
   wherein said first independently replicating element is selected from the two plasmids pPGtrpRopAp or pPGtrpRopTc, wherein said site for insertion of a gene that is included in the said first element contains a gene to be expressed, and
   wherein said second independently replicating element is the other of said two plasmids, pPGtrpRopAp or pPGtrpRopTc, selected as said first independently replicating element wherein the Rop encoding gene is intact.

2. A procaryotic cell comprising the expression system according to claim 1.

3. The cell according to claim 3 wherein said cell is a bacterial cell.

4. The cell according to claim 3 wherein said bacterial cell is an *E. coli* cell.

* * * * *